(12) United States Patent
Van Heugten et al.

(10) Patent No.: US 9,107,612 B2
(45) Date of Patent: *Aug. 18, 2015

(54) INTEGRATED SURGICAL MICROSCOPE AND WAVEFRONT SENSOR

(71) Applicant: WaveTec Vision Systems, Inc., Aliso Viejo, CA (US)

(72) Inventors: Anthony Y. Van Heugten, Sarasota, FL (US); Daniel S. Durrie, Overland Park, KS (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/797,365

(22) Filed: Mar. 12, 2013

(65) Prior Publication Data
US 2013/0335705 A1    Dec. 19, 2013

Related U.S. Application Data

(63) Continuation of application No. 13/619,168, filed on Sep. 14, 2012, now Pat. No. 8,475,439, which is a
(Continued)

(51) Int. Cl.
*A61B 18/18* (2006.01)
*A61B 3/103* (2006.01)
(Continued)

(52) U.S. Cl.
CPC ............... *A61B 3/103* (2013.01); *A61B 19/52* (2013.01); *A61F 9/007* (2013.01); *A61F 9/008* (2013.01);
(Continued)

(58) Field of Classification Search
CPC ................................ A61B 3/1015; A61B 3/14

USPC ........................................ 351/205; 606/4, 5
See application file for complete search history.

(56) References Cited

U.S. PATENT DOCUMENTS

| 3,947,186 A | 3/1976 | Howland |
| 4,019,813 A | 4/1977 | Cornsweet et al. |

(Continued)

FOREIGN PATENT DOCUMENTS

| AU | 2005234778 | 8/2011 |
| CA | 2521845 | 11/2004 |

(Continued)

OTHER PUBLICATIONS

Combined International Search Report and Written Opinion of the International Searching Authority for International Application No. PCT/US05/13550; issued by the ISA/US; dated Nov. 15, 2005.
(Continued)

*Primary Examiner* — William Thomson
*Assistant Examiner* — Jeffrey Lipitz
(74) *Attorney, Agent, or Firm* — Knobbe, Martens Olson & Bear, LLP

(57) ABSTRACT

A wavefront sensor is integrated with a surgical microscope for allowing a doctor to make repeated wavefront measurements of a patient's eye while the patient remains on an operating table in the surgical position. The device includes a wavefront sensor optically aligned with a surgical microscope such that their fields of view at least partially overlap. The inclusion of lightweight, compact diffractive optical components in the wavefront sensor allows the integrated device to be supported on a balancing mechanism above a patient's head during a surgical procedure. As a result, the need to reposition the device and/or the patient between measuring optical properties of the eye and performing surgical procedures on the eye is eliminated. Many surgical procedures may be improved or enhanced using the integrated device, including but not limited to cataract surgery, Conductive Keratoplasty, Lasik surgery, and corneal corrective surgery.

14 Claims, 5 Drawing Sheets

Related U.S. Application Data continuation of application No. 13/021,594, filed on Feb. 4, 2011, now Pat. No. 8,394,083, which is a continuation of application No. 11/110,653, filed on Apr. 20, 2005, now Pat. No. 7,883,505.

(60) Provisional application No. 60/563,727, filed on Apr. 20, 2004.

(51) Int. Cl.
  *A61B 19/00* (2006.01)
  *A61F 9/007* (2006.01)
  *A61F 9/008* (2006.01)
  *A61F 9/013* (2006.01)
  *A61B 3/10* (2006.01)

(52) U.S. Cl.
  CPC ............ *A61F 9/0081* (2013.01); *A61F 9/00827* (2013.01); *A61F 9/013* (2013.01); *A61B 3/1015* (2013.01); *A61B 19/5223* (2013.01); *A61F 9/00736* (2013.01); *A61F 9/00831* (2013.01); *A61F 9/00834* (2013.01); *A61F 2009/00842* (2013.01); *A61F 2009/00848* (2013.01); *A61F 2009/00853* (2013.01); *A61F 2009/00868* (2013.01); *A61F 2009/00872* (2013.01); *A61F 2009/00887* (2013.01)

(56) References Cited

U.S. PATENT DOCUMENTS

| | | |
|---|---|---|
| 4,125,320 A | 11/1978 | Rassow |
| 4,172,662 A | 10/1979 | Vogel |
| 4,173,398 A | 11/1979 | Okamoto et al. |
| 4,293,198 A | 10/1981 | Kohayakawa et al. |
| 4,353,625 A | 10/1982 | Nohda et al. |
| 4,372,655 A | 2/1983 | Matsumura et al. |
| 4,376,573 A | 3/1983 | Matsumura et al. |
| 4,390,255 A | 6/1983 | Nohda et al. |
| 4,421,391 A | 12/1983 | Matsumura et al. |
| 4,459,027 A | 7/1984 | Kafri et al. |
| 4,541,697 A | 9/1985 | Ramijan |
| 4,640,596 A | 2/1987 | Humphrey |
| 4,650,301 A | 3/1987 | Humphrey |
| 4,669,835 A | 6/1987 | Humphrey |
| 4,692,003 A | 9/1987 | Adachi et al. |
| 4,710,193 A | 12/1987 | Volk |
| 4,721,379 A | 1/1988 | L'Esperance |
| 4,730,917 A | 3/1988 | Krueger |
| 4,911,711 A | 3/1990 | Telfair et al. |
| 4,964,715 A | 10/1990 | Richards |
| 4,984,883 A | 1/1991 | Winocur |
| 4,995,716 A | 2/1991 | Warnicki et al. |
| 5,080,477 A | 1/1992 | Adachi |
| 5,144,478 A | 9/1992 | Toshimitsu |
| 5,157,427 A | 10/1992 | Humphrey |
| 5,164,750 A | 11/1992 | Adachi |
| 5,202,708 A | 4/1993 | Sasaki et al. |
| 5,206,672 A | 4/1993 | Rowe |
| 5,208,619 A | 5/1993 | Campbell |
| 5,223,863 A | 6/1993 | Heine |
| 5,252,999 A | 10/1993 | Sukigara |
| 5,258,791 A | 11/1993 | Penny et al. |
| 5,270,749 A | 12/1993 | Okamura |
| 5,282,852 A | 2/1994 | Capetan et al. |
| 5,294,971 A | 3/1994 | Braunecker et al. |
| 5,307,097 A | 4/1994 | Baker |
| 5,329,322 A | 7/1994 | Yancey |
| 5,374,193 A | 12/1994 | Trachtman |
| 5,450,143 A | 9/1995 | Rowe et al. |
| 5,455,645 A | 10/1995 | Berger et al. |
| 5,493,109 A | 2/1996 | Wei et al. |
| 5,576,780 A | 11/1996 | Yancey |
| 5,777,719 A | 7/1998 | Williams et al. |
| 5,796,463 A | 8/1998 | Bullimore |
| 5,800,533 A | 9/1998 | Eggleston et al. |
| 5,841,511 A | 11/1998 | D'Souza et al. |
| 5,861,937 A | 1/1999 | Fujieda |
| 5,909,268 A | 6/1999 | Isogai et al. |
| 5,936,706 A | 8/1999 | Takagi |
| 5,949,521 A | 9/1999 | Williams et al. |
| 5,963,300 A | 10/1999 | Horwitz |
| 5,968,094 A | 10/1999 | Werblin et al. |
| 5,968,095 A | 10/1999 | Norrby |
| 5,994,687 A | 11/1999 | Chanteloup et al. |
| 6,002,484 A | 12/1999 | Rozema et al. |
| 6,004,313 A | 12/1999 | Shimmick et al. |
| 6,007,204 A | 12/1999 | Fahrenkrug et al. |
| 6,042,232 A | 3/2000 | Luce et al. |
| 6,043,885 A | 3/2000 | Mazuet et al. |
| 6,050,687 A | 4/2000 | Bille et al. |
| 6,086,204 A | 7/2000 | Magnante |
| 6,095,651 A | 8/2000 | Williams et al. |
| 6,096,077 A | 8/2000 | Callahan et al. |
| 6,155,684 A | 12/2000 | Bille et al. |
| 6,199,986 B1 | 3/2001 | Williams et al. |
| 6,251,101 B1 | 6/2001 | Glockler |
| 6,262,328 B1 | 7/2001 | Wicks et al. |
| 6,264,328 B1 | 7/2001 | Williams et al. |
| 6,270,221 B1 | 8/2001 | Liang et al. |
| 6,271,915 B1 | 8/2001 | Frey et al. |
| 6,275,718 B1 | 8/2001 | Lempert |
| 6,299,311 B1 | 10/2001 | Williams et al. |
| 6,299,618 B1 | 10/2001 | Sugiura |
| 6,338,559 B1 | 1/2002 | Williams et al. |
| 6,379,005 B1 | 4/2002 | Williams et al. |
| 6,382,793 B1 | 5/2002 | Lai et al. |
| 6,382,794 B1 | 5/2002 | Lai et al. |
| 6,382,795 B1 | 5/2002 | Lai |
| 6,394,605 B1 | 5/2002 | Campin et al. |
| 6,409,345 B1 | 6/2002 | Molebny et al. |
| 6,419,671 B1 | 7/2002 | Lemberg |
| 6,439,720 B1 | 8/2002 | Graves et al. |
| 6,460,997 B1 | 10/2002 | Frey et al. |
| 6,497,483 B2 | 12/2002 | Frey et al. |
| 6,508,812 B1 | 1/2003 | Williams et al. |
| 6,511,180 B2 | 1/2003 | Guirao et al. |
| 6,550,917 B1 | 4/2003 | Neal et al. |
| 6,561,648 B2 | 5/2003 | Thomas |
| 6,570,143 B1 | 5/2003 | Neil et al. |
| 6,572,230 B2 | 6/2003 | Levine |
| 6,575,572 B2 | 6/2003 | Lai et al. |
| 6,578,963 B2 | 6/2003 | Pettit |
| 6,585,723 B1 | 7/2003 | Sumiya |
| 6,588,902 B2 | 7/2003 | Isogai |
| 6,598,975 B2 | 7/2003 | Liang et al. |
| 6,601,956 B1 | 8/2003 | Jean et al. |
| 6,609,793 B2 | 8/2003 | Norrby et al. |
| 6,609,794 B2 | 8/2003 | Levine |
| 6,626,535 B2 | 9/2003 | Altmann |
| 6,626,538 B1 | 9/2003 | Arrowsmith |
| 6,634,751 B2 | 10/2003 | Turner et al. |
| 6,637,884 B2 | 10/2003 | Martino |
| 6,658,282 B1 | 12/2003 | Eagan et al. |
| 6,679,606 B2 | 1/2004 | Campin et al. |
| 6,685,319 B2 | 2/2004 | Watson et al. |
| 6,702,806 B2 | 3/2004 | Gray et al. |
| 6,705,729 B2 | 3/2004 | Piers et al. |
| 6,724,464 B2 | 4/2004 | Yang et al. |
| 6,736,509 B2 | 5/2004 | Martino et al. |
| 6,736,510 B1 | 5/2004 | Van Heugten |
| 6,739,721 B2 | 5/2004 | Altmann |
| 6,761,454 B2 | 7/2004 | Lai et al. |
| 6,781,681 B2 | 8/2004 | Horwitz |
| 6,786,603 B2 | 9/2004 | Altmann |
| 6,793,654 B2 | 9/2004 | Lemberg |
| 6,819,413 B2 | 11/2004 | Neal et al. |
| 6,827,444 B2 | 12/2004 | Williams et al. |
| 6,836,374 B2 | 12/2004 | Esch et al. |
| 6,905,641 B2 | 6/2005 | Platt et al. |
| 6,908,196 B2 | 6/2005 | Herekar et al. |
| 6,926,710 B2 | 8/2005 | Cox et al. |
| 6,948,818 B2 | 9/2005 | Williams et al. |

(56) References Cited

U.S. PATENT DOCUMENTS

| | | |
|---|---|---|
| 6,997,555 B2 | 2/2006 | Dick et al. |
| 7,018,376 B2 | 3/2006 | Webb |
| 7,034,949 B2 | 4/2006 | Horwitz |
| 7,044,602 B2 | 5/2006 | Chernyak |
| 7,044,604 B1 | 5/2006 | Arrowsmith |
| 7,057,806 B2 | 6/2006 | Atkinson |
| 7,066,928 B2 | 6/2006 | Dick et al. |
| 7,068,439 B2 | 6/2006 | Esch et al. |
| 7,070,276 B2 | 7/2006 | Koretz |
| 7,077,522 B2 | 7/2006 | Williams |
| 7,111,938 B2 | 9/2006 | Andino et al. |
| 7,182,780 B2 | 2/2007 | Terwee et al. |
| 7,237,898 B1 | 7/2007 | Hohla et al. |
| 7,255,442 B2 | 8/2007 | Bucourt et al. |
| 7,303,281 B2 | 12/2007 | Wakil et al. |
| 7,336,371 B1 | 2/2008 | Haidner et al. |
| 7,341,348 B2 | 3/2008 | Eagan |
| 7,350,916 B2 | 4/2008 | Hong et al. |
| 7,350,920 B2 | 4/2008 | Levine |
| 7,357,509 B2 | 4/2008 | Williams et al. |
| 7,374,286 B2 | 5/2008 | Fujieda et al. |
| 7,377,641 B2 | 5/2008 | Piers et al. |
| 7,380,942 B2 | 6/2008 | Molebny et al. |
| 7,401,919 B2 | 7/2008 | Vogelsang et al. |
| 7,406,263 B2 | 7/2008 | Graves et al. |
| 7,416,305 B2 | 8/2008 | Williams et al. |
| 7,425,067 B2 | 9/2008 | Warden et al. |
| 7,441,901 B2 | 10/2008 | Liang |
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |
| 8,313,196 B2 | 11/2012 | Ianchulev |
| 8,333,474 B2 | 12/2012 | Michaels et al. |
| 8,480,659 B2 | 7/2013 | Frey et al. |
| 8,545,023 B2 | 10/2013 | Holladay et al. |
| 8,550,624 B2 | 10/2013 | Padrick et al. |
| 8,619,405 B2 | 12/2013 | Van Heugten |
| 8,632,185 B2 | 1/2014 | Ianchulev |
| 8,764,187 B2 | 7/2014 | Padrick et al. |
| 8,876,290 B2 | 11/2014 | Sarver et al. |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0097376 A1 | 7/2002 | Applegate et al. |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0133228 A1 | 9/2002 | Sarver |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1* | 1/2003 | Levine .......... 351/206 |
| 2003/0007127 A1 | 1/2003 | Levine |
| 2003/0009156 A1 | 1/2003 | Levine |
| 2003/0025080 A1* | 2/2003 | Sting et al. .......... 250/339.07 |
| 2003/0053025 A1 | 3/2003 | Turner et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli |
| 2005/0068497 A1 | 3/2005 | Hanebuchi et al. |
| 2005/0105044 A1 | 5/2005 | Warden et al. |
| 2005/0110946 A1 | 5/2005 | Youssefi et al. |
| 2005/0110949 A1 | 5/2005 | Goldfain et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1* | 1/2006 | Mayo et al. .......... 351/205 |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0247659 A1 | 11/2006 | Moeller et al. |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0070293 A1 | 3/2007 | Isogai |
| 2007/0083261 A1 | 4/2007 | Colvard |
| 2007/0115432 A1 | 5/2007 | Thibos |
| 2007/0236702 A1 | 10/2007 | Neal et al. |
| 2007/0260157 A1 | 11/2007 | Norrby |
| 2008/0004610 A1 | 1/2008 | Miller et al. |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0009717 A1 | 1/2009 | Barrett et al. |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0036386 A1 | 2/2010 | Ianchulev |
| 2010/0042210 A1 | 2/2010 | Ianchulev |
| 2010/0152847 A1 | 6/2010 | Padrick et al. |
| 2011/0001960 A1 | 1/2011 | Van Heugten |
| 2011/0007270 A1 | 1/2011 | Sarver |
| 2011/0013141 A1 | 1/2011 | Holladay et al. |
| 2011/0015541 A1 | 1/2011 | Padrick |
| 2011/0242482 A1 | 10/2011 | Olsen |
| 2011/0267579 A1 | 11/2011 | Van Heugten |
| 2012/0147460 A1 | 6/2012 | Kubler |
| 2013/0021574 A1 | 1/2013 | Van Heugten |
| 2013/0070203 A1 | 3/2013 | Michaels |
| 2013/0131687 A1 | 5/2013 | Lanchulev |
| 2014/0085604 A1 | 3/2014 | Michaels |
| 2014/0111772 A1 | 4/2014 | Ikegami |

(56) References Cited

U.S. PATENT DOCUMENTS

| | | | |
|---|---|---|---|
| 2014/0132922 A1 | 5/2014 | Padrick |
| 2014/0132931 A1 | 5/2014 | Holladay |
| 2014/0249624 A1 | 9/2014 | Ianchulev |
| 2014/0313487 A1 | 10/2014 | Heugten |

FOREIGN PATENT DOCUMENTS

| | | | |
|---|---|---|---|
| CA | 2515010 | | 5/2013 |
| CN | 1942146 | A | 4/2007 |
| CN | 102497833 | A | 6/2012 |
| DE | 43 10 561 | A1 | 9/1994 |
| DE | 19 85 7001 | A1 | 6/2000 |
| EP | 0931504 | A1 | 7/1999 |
| EP | 2444021 | | 4/2012 |
| EP | 2453822 | | 5/2012 |
| EP | 2453823 | | 5/2012 |
| EP | 1596710 | | 1/2013 |
| EP | 1 737 372 | | 8/2014 |
| EP | 2 818 130 | | 12/2014 |
| GB | 1 209 451 | | 10/1970 |
| IL | 138282 | | 7/2004 |
| JP | 11-24434 | | 5/1989 |
| JP | 9-122075 | | 5/1997 |
| JP | 10-272100 | | 10/1998 |
| JP | 2000-139996 | | 5/2000 |
| JP | 2000-197607 | | 7/2000 |
| JP | 2001-507258 | A | 6/2001 |
| JP | 2001-314372 | A | 11/2001 |
| JP | 2002-306418 | A | 10/2002 |
| JP | 2003-509731 | A | 3/2003 |
| JP | 2003-102689 | A | 4/2003 |
| JP | 4972546 | | 4/2012 |
| WO | WO 92/01417 | | 2/1992 |
| WO | WO 96/22506 | | 7/1996 |
| WO | WO 98/27863 | | 7/1998 |
| WO | WO 00/33729 | | 6/2000 |
| WO | WO 01/06914 | | 2/2001 |
| WO | WO 01/21061 | | 3/2001 |
| WO | WO 01/26591 | | 4/2001 |
| WO | WO 01/58339 | | 8/2001 |
| WO | WO 02/17775 | | 3/2002 |
| WO | WO 03/050472 | | 6/2003 |
| WO | WO 03/102498 | | 12/2003 |
| WO | WO 2004/093663 | | 11/2004 |
| WO | WO 2005/057252 | | 6/2005 |
| WO | WO 2006/081031 | | 8/2006 |
| WO | WO 2009/086059 | | 7/2009 |
| WO | WO 2014/052479 | | 4/2014 |
| WO | WO 2014/052478 | | 6/2014 |

OTHER PUBLICATIONS

Restriction Requirement issued on Apr. 10, 2007 in U.S. Appl. No. 10/820,635, filed Apr. 8, 2004.
Response to Restriction Requirement filed on May 3, 2007, in U.S. Appl. No. 10/820,635, filed Apr. 8, 2004.
Non-Final Office Action issued on Jul. 11, 2007 in U.S. Appl. No. 10/820,635, filed Apr. 8, 2004.
Office Action Response filed on Jan. 11, 2008 U.S. Appl. No. 10/820,635, filed Apr. 8, 2004.
Final Office Action issued on Apr. 10, 2008 in U.S. Appl. No. 10/820,635, filed Apr. 8, 2004.
Office Action mailed May 30, 2008 in Chinese Patent Application 200580011803.6 filed Apr. 20, 2005.
Request for Continued Examination and Amendment filed on May 11, 2009 in U.S. Appl. No. 10/820,635, filed Apr. 8, 2004.
Office Action mailed May 15, 2009 in Japanese Patent Application 2001-511810 filed Jul. 27, 1999.
Office Action mailed May 22, 2009 in Chinese Patent Application 200580011803.6 filed Apr. 20, 2005.
Notice of Allowance issued on May 26, 2009 in U.S. Appl. No. 10/820,635, filed Apr. 8, 2004.
Office Action mailed Jun. 2, 2009, issued in U.S. Appl. No. 11/110,653, filed Apr. 20, 2005.
Office Action mailed Jul. 7, 2009, in U.S. Appl. No. 11/110,968, filed Apr. 20, 2005.
Rejection Decision issued Aug. 14, 2009 in Chinese Patent Application No. 2004-80003472.7 filed Jan. 20, 2004.
Office Action issued on Sep. 10, 2010 in in U.S. Appl. No. 12/499,079, filed Jul. 7, 2009.
Preliminary Amendment filed Oct. 15, 2009 in U.S. Appl. No. 12/499,079, filed Jul. 7, 2009.
Office Action Response filed Dec. 1, 2009 in U.S. Appl. No. 11/110,653, filed Apr. 20, 2005.
Office action mailed Dec. 14, 2009 in European Patent Application 04703599.3 filed Jan. 20, 2004.
Office action mailed Dec. 18, 2009 in Japanese Patent Application 2006-502878 filed Jan. 20, 2004.
Office Action mailed Dec. 25, 2009 in Chinese Patent Application 200580011803.6 filed Apr. 20, 2005.
Office Action Response filed Jan. 7, 2010 in U.S. Appl. No. 11/110,968, filed Apr. 20, 2005.
Office Action mailed Jan. 15, 2010, issued in European Application No. 05737636.0 filed Apr. 20, 2005.
Final Office Action mailed Feb. 1, 2010 in U.S. Appl. No. 11/110,653, filed Apr. 20, 2005.
Office Action mailed Feb. 9, 2010 in Japanese Patent Application 2001-511810 filed Jul. 27, 1999.
International Search Report and Written Opinion for International Application No. PCT/US2009/063651 mailed Mar. 9, 2010.
Office Action issued on Apr. 6, 2010 in corresponding Australian Patent Application No. 2005234778.
International Search Report and Written Opinion, issued Apr. 30, 2010 in related International Patent Application No. PCT/US08/81584, filed Oct. 29, 2008.
RCE and Amendment filed Jul. 30, 2010 in U.S. Appl. No. 11/110,653, filed Apr. 20, 2005.
Notice of Allowance issued Sep. 28, 2010 in U.S. Appl. No. 11/110.653, filed Apr. 20, 2005.
International Search Report and Written Opinion mailed Oct. 7, 2010 for International Application No. PCT/US2010/041229.
International Search Report and Written Opinion mailed Oct. 7, 2010 for International Application No. PCT/US2010/041242.
Final Office Action mailed Oct. 29, 2010 in U.S. Appl. No. 11/110,968, filed Apr. 20, 2005.
Office Action dated Nov. 2, 2010 in Japanese Application No. 2007-509613 (with English Translation).
Response to Office Action dated Nov. 2, 2010 filed in corresponding Japanese Application No. JP 2007-509613, on Apr. 4, 2011.
Office Action mailed Feb. 28, 2011 in U.S. Appl. No. 12/581,061, filed Oct. 16, 2009.
Office Action mailed Feb. 20, 2009 in Chinese Patent Application No. 2004-80003472.7 filed Jan. 20, 2004.
Amendment filed on Mar. 9, 2011 in U.S. Appl. No. 12/499,079, filed Jul. 7, 2009.
Notice of Allowance issued on Mar. 22, 2011 in U.S. Appl. No. 12/499,079, filed Jul. 7, 2009.
Office Action mailed in corresponding European Patent Application No. 04703 599.3 on Mar. 23, 2011
Request for Continued Examination, Final Amendment and Summary of Interview, filed in corresponding U.S. Appl. No. 11/110,968 on Apr. 29, 2011.
Response to Office Action filed in corresponding U.S. Appl. No. 12/206,974 on May 10, 2011.
English Translation of Office Action mailed May 13, 2011 in corresponding Japanese Application No. JP 2006-502878.
Response to Office Action filed in corresponding U.S. Appl. No. 12/581,061 on Jun. 28, 2011.
Preliminary Amendment filed Jul. 19, 2011 in corresponding U.S. Appl. No. 13/021,594.
Final Office Action issued on Aug. 2, 2011 in corresponging U.S. Appl. No. 12/206,974.
Final Office Action issued on Sep. 6, 2011 in corresponding U.S. Appl. No. 12/581,061.

(56) References Cited

OTHER PUBLICATIONS

Response to Office Action filed in corresponding European Patent Application No. 04703 599.3 on Sep. 22, 2011.
Notification of Reasons for Refusal mailed in corresponding Japanese Patent Application No. JP 2007-509613 on Oct. 11, 2011.
Office Action issued in corresponding European Patent Application No. 05737636 on Oct. 27, 2011.
Request for Continued Examination, Final Amendment and Summary of Interview, filed in corresponding U.S. Appl. No. 12/206,974 on Dec. 2, 2011.
Office Action issued Jan. 17, 2012 in connection with Canadian Patent Application No. 2,515,010.
Office Action mailed on Jan. 25, 2012 in corresponding U.S. Appl. No. 13/021,594, filed Feb. 4, 2011.
Supplemental Preliminary Amendment filed Feb. 1, 2012 in U.S Appl. 13/363,287, filed Jan. 31, 2012.
Response to Office Action filed in connection with European European Patent Application No. 05737636 on Feb. 27, 2012.
Request for Continued Examination, Amendment and Terminal Disclaimer filed in connection with U.S. Appl. No. 12/581,061 on Mar. 5, 2012.
Response to Office Action filed in corresponding Japanese Application No. JP 2007-509613, on Mar. 8, 2012.
Decision to Grant issued on Mar. 13, 2012 in connection with Japanese Patent Application No. 2007-509613.
Notice of Allowance issued on Mar. 20, 2011 in connection with U.S. Appl. No. 12/581,061 on Mar. 5, 2012.
Request for Continued Examination and IDS filed in connection with U.S. Appl. No. 12/206,974 on Mar. 21, 2012.
Notice of Allowance issued in corresponding U.S. Appl. No. 12/206,974 on Dec. 22, 2011.
Extended Search Report issued on Mar. 26, 2012 in connection with European Patent Application No. 12151139.8.
Office Action issued on Mar. 26, 2012 in connection with European Application No. EP 05737636.
Office Action issued on May 16, 2012 in connection with U.S. Appl. No. 12/614,344, filed Nov. 6, 2009.
Response to Office Action filed on May 22, 2012 in corresponding U.S. Appl. No. 13/021,594.
Response to Restriction Requirement filed on Jul. 6, 2012 in corresponding U.S. Appl. No. 12/835,665.
Notice of Allowance issued on Jul. 11, 2012 in corresponding U.S. Appl. No. 13/021,594.
Notice of Allowance issued on Jul. 18, 2012 in corresponding U.S. Appl. No. 12/581,061.
Notice of Allowance issued on Aug. 6, 2012 in connection with corresponding U.S. Appl. No. 12/206,974, filed Sep. 9, 2008.
Non-Final Office Action issued on Aug. 24, 2012 in corresponding U.S. Appl. No. 12/835,668.
Preliminary Amendment filed on Sep. 14, 2012 in corresponding U.S. Appl. No. 13/750,080.
Notice of Allowance issued on Sep. 17, 2012 in corresponding Canadian Application No. CA 2,515,010.
Response to Office Action dated Mar. 26, 2012, mailed on Oct. 4, 2012 in corresponding Application No. EP 05737636.
Non-Final Office Action issued on Oct. 5, 2012 in U.S. Appl. No. 12/835,665.
Request for Continued Examination filed on Oct. 10, 2012 in corresponding U.S. Appl. No. 13/021,594.
Office Action issued on Oct. 25, 2012 in connection with corresponding U.S. Appl. No. 12/581,074.
Office Action issued on Oct. 26, 2012 in connection with corresponding U.S. Appl. No. 13/619,168.
Notice of Allowance issued on Oct. 30, 2012 in connection with corresponding U.S. Appl. No. 13/021,594.
Office Action issued on Nov. 5, 2012 in connection with corresponding U.S. Appl. No. 12/830,221.
Preliminary Amendment filed on Dec. 3, 2012 in corresponding U.S. Appl. No. 13/620,593.
Response to Office Action filed Dec. 10, 2012 in corresponding U.S. Appl. No. 12/740,753.
Office Action issued on Dec. 17, 2012 in corresponding U.S Appl. No. 12/614,344.
Extended Search Report issued on Jan. 8, 2013 in connection with European Patent Application No. 10800335.
Response to Office Action filed Jan. 25, 2013 in connection with related U.S. Appl. No. 12/581,074.
Office Action issued on Feb. 12, 2013 in connection with related Canadian Patent Application No. 2,561,388.
Final Office Action, issued on Feb. 19, 2013, in corresponding U.S. Appl. No. 12/835,668.
Office Action issued on Apr. 4, 2013, in corresponding EP Application No. 12 151 139.8.
Office Action issued May 9, 2013 in connection with U.S. Appl. No. 12/581,074.
Notice of Allowance issued on May 16, 2013 in corresponding U.S. Appl. No. 13/619,787.
Request for Continued Examination and Response to Office Action filed Aug. 9, 2013 in corresponding U.S. Appl. No. 12/581,074.
Notice of Allowance issued on Feb. 20, 2014 in corresponding U.S. Appl. No. 12/835,668.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations," http://doctor-hill.com/iol-mail/piggyback.html, accessed on Feb. 12, 2010.
Aramberri, "Intraocular lens power calculation after corneal infrastructure surgery: Double-K method," J Cataract Refract Surg 29:2063-2068 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "Power of the Pre-Pupillary Pseudoshakos," B.J.O. 56:332-37 (1972).
Binkhorst, "The Optical Design of the Intraocular Lens Implants," Opthalmic Surg 6(3): 17-31 (1975).
Brandser R., "Accuracy of IOL calculation in cataract surgery", Acta Ophthalmol Scand. Apr. 1997; 75(2)162-5 (Abstract).
Castro et al., "Tilt and decentration of intraocular lenses in vivo from Purkinje and Scheimpflug imaging: Validation study," J. Cataract Refract. Surg. 2007; 33:418-429.
Chen et al., "Analysis of intraocular lens power calculation in post-radial keratotomy eyes," J Cataract Refract Surg 29:65-? (Jan. 2003).
Colenbrander, "Calculation of the Power of an Iris-Clip Lens for Distance Vision," Br. J. Ophthal. 57:735-40(1973).
Cordonnier, M., et al., "How accurate is the hand-held refractor Retinomax(R) in measuring cycloplegic refraction: a further evaluation", Strabismus. Sep. 1998;6(3):133-142 (Abstract).
Cua at al., Intraocular lens calculations in patients with corneal scarring and irregular astigmatism, J Cataract Refract Surg 29:1352-1357 (Jul. 2003).
Dalens H, Marcellier JJ, Moussiere L., "Use of the SRK (Sanders-Retzlaff-Kraft) regression formula in the preoperative calculation of the power of crystalline implants" (Abstract).
Donoso R., et al., "Emmetropization at cataract surgery. Looking for the best IOL power calculation formula according to the eye length", Arch Soc Esp Oftalmol. Sep. 2003;78(9):477-80 (Abstract).
El-Baha SM, et al., "Intraoperative biometry for intraocular lens (IOL) power calculation at silicone oil removal", Eur J Ophthalmol. Aug.-Sep. 2003;13(7):622-6 (Abstract).
Ei-Defrawy S., et al. "Evaluation of a hand-held autorefractor in children younger than 6", J Pediatr Ophthalmol Strabismus, 1998 ~ar-Apr.;35(2):107-9 (Abstract).
Feiz, et al., "Intraocular Lens Power Calculation After Laser In Situ Keratomileusis for Myopia and Hyperopia—A Standard Approach," Cornea 20(8):792-797 (2001).
Feordorov et al. "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia 2003;56(1):11-4 (Abstract).

(56) References Cited

OTHER PUBLICATIONS

Gernet, "IOL Calculation According to Gernet and the GOW 70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001).
Gimbel et al., "Accuracy and Predictability of Intraocular Lens Power Calculation After photorefractive keratectomy," J Cataract Refract Surg 26:1147-1151 (Apr. 2000).
Gupta, et al., *"Design and use of an infrared Pupilometer for real-time pupil mapping in response to incremental illumination levels,"* 2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/ArticleStandard/Article/detail/559856.
Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden Intraokularlinse" [Intraoperative retinoscopy for determining the refractive value of an implantable intraocular lens] Klin. Monatsbl. Augenheilkd. vol. 210, No. 4, 1997, pp. 207-212.
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," J. Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions. CLAO J. 1984, 10:326-31.
Holladay, JT, et al. "Calculating the Surgically Induced Refractive Change Following Ocular Surgery", J. Cataract Refract. Surg. 1992; 18:429-43.
http://www.wavetecvision.com/ accessed Feb. 24, 2010.
Hunt et al., "Evaluation of the measurement of refractive error by the PowerRefractor: a remote, continuous and binocular measurement system of oculomotor function," Br. J. Opthalmol 87:1504-1508 (2003).
Ianchulev, "Method for Intraoperative Refractive IOL Calculation," Poster Presentation at Ophthalmology Conference (Apr. 2004).
Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536, Abstract.
Isenberg et al., "Use of the HARK Autorefractor in Children," American Journal of Ophthalmology 131(4):438-441 (2001).
Iuorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).
Ivanov MN, et al., "Formula for calculating the IOL focal power", Vestn Oftalmol. Jul.-Aug. 2003:119 (4):52-4 (Abstract).
Iwami S. et al., "Prediction of Postoperative Refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and LASIK", Korean J Ophthalmol. Jun. 2002;16(1):26-31 (Abstract).

Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).
Liang, et al. "Aberrations and Retinal Image Quality of the Normal Human Eye", J. Optical Society of America, vol. 14, No. 11, Nov. 1997.
Liang, et al. "Comparison of Measurements of Refractive Errors Between the Hand-held Retinomax and On-table Autorefractors in Cycloplegded and Noncyclopleged Children," American Journal of Ophthalmology 136(6): 1120-1128 (Dec. 2003).
Lipatov DV., "Assessment of the efficiency of different formulae applied to calculating the optic power of an intraocular lens in trans-scleral fixation", Vestn Oftalmol, Nov.-Dec. 2003; 119(6):33-5 (Abstract).
Ma, et al., "Simple method for accurate alignment in toric phakic and aphakic intraocular lens implantation," J Cataract Refract Surg, Technique, Oct. 2008, vol. 34, pp. 1631-1636.
Mackool RJ., "The cataract extraction-refraction-implantation technique for IOL power calculation in difficult cases", J Cataract Refract Surg. Apr. 1998;24(4):434-5 (Abstract).
Masket, et al., "Atlas of Cataract Surgery," Book cover in 1 page, Front Matter in 11 pages (Table of Contents in 3 pages), Chapter 19 pp. 147-158, Published by Martin Dunitz Ltd 1999, United Kingdom.
Methling D, Kalb G., "A New Program for Calculating Intraocular Lenses", Klin Monatsbl Augenheilkd. Oct. 1992;201 (4):247-53 (Abstract).
Moreno-Barriuso, et al., "Laser Ray Tracing Versus Hartmann-Shack Sensor for Measuring Optical Aberrations in the Human Eye", J. Optical Society of America, vol. 17, No. 6, Jun. 2000.
Nemeth et al., "Optical and ultrasound measurement of axial length and anterior chamber depth for intraocular lens power calculation," J Cataract Refract Surg 29:85-88 (Jan. 2003).
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001).
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Photograph of Oculus Instrument, accessed at http://www.oculus.de/en/sites/popup_bild_gross.php?news=&id=1056 on Apr. 29, 2011.
Quiroga, et al., *"Fourier transform method for automatic processing of moire deflectograms,"* Jun. 1999, Society of Photo-Optical Instrumentation Engineers, pp. 974-982.
Raj et al., "Clinical evaluation of automated refractio in anterior chamber pseudophakia," British Journal of Ophthalmology 75:42-44 (1991).
Raj et al., "Objective autorefraction in posterior chamber pseudophakia," British Journal of Ophthalmology 74:731-733 (1990).
Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).
Retzlaff J., "A new intraocular lens calculation formula", J Am Intraocul Implant Soc. Apr. 1980 6(2):148-52. (Abstract).
Rosales et al., "Phakometry and lens tilt and decentration using a custom-developed Purkinje imaging apparatus: validation and measurements," Journal of the Optical Society of America, vol. 23, No. 3, Mar. 2006. pp. 509-520.
Rubin A., et al., "Refractive variation during autorefraction: multivariate distribution of refractive status", Optom Vis Sci. Jun. 1995;72(6):403-10 (Abstract).
Rubin A., et al., "Variation during autorefraction: influence of two different target types", Ophthalmic Physiol Opt. Jan. 1997;17(1):38-43 (Abstract).

(56) References Cited

OTHER PUBLICATIONS

Sanders et al., "Comparison of the SRK/T formula and other theoretical and regression formulas," J Cataract Refract Surg. 16:341-346 (May 1990).
Sanders et al., "Comparisons of the SRK™ formula and other second generation formulas," J Cataract Refract Surg 14;136-141 (Mar. 1988).
Senjo, et al., "Prediction of Postoperative Refraction Using Intraoperative Retinoscopy," Journal of Japanese Ophthalmological Society, 1999, vol. 103, No. 7, pp. 551-555, Abstract.
Siahmed K., et al., "Optic biometry in intraocular lense calculation for cataract surgery. Comparison with usual methods", J Fr Ophthalmol. Nov. 2001;24(9):922-6 (Abstract).
Siganos et al., "Autorefractometry after laser in situ keratomileusis," J Cataract Refract Surg 29:133-137 (Jan. 2003).
Supplemental Amendment filed Apr. 1, 2010 in U.S Appl. 11/110,968, filed Apr. 20, 2005.
Supplementary European Search Report for Application No. 05737636.0, Dated Mar. 19, 2009.
Steele, G., et al., "Cycloplegic auto refraction results in pre-school children using the Nikon Retinomax Plus and the Welch Allyn SureSight", Optom Vis Sci. Aug. 2003;80(8):573-7 (Abstract).
Straub et al., *"Design of a compact Shack-Hartmann aberrometr for real-time measurement of aberrations in human eyes,"* 2000 Optical Society of America, pp. 110-113.
Suto et al., "Adjusting intraocular lens power for sulcus fixation," J Cataract Refract Surg 29:1913-1917 (Oct. 2003).
Tabernero et al., "Instrument for measuring the misalignments of the ocular surfaces," Optical Society of Maerica, Oct. 30, 2006, vol. 14, No. 22.
Thall et al., "Linear Regression Software for Intraocular Lens Implant Power Calculation," American Journal of Ophthalmology 101:597-599 (May 1986).
Thijssen JM., "The emmetropic and the iseikonic implant lens; computer calculation of the' refractive power and its accuracy", Ophthalmologica 1975;171 (6):467-86 (Abstract).
Thompson et al., "A New Posterior Chamber Intraocular Lens Formula for Axial Myopes," Ophthalmology 91(5): 484-488 (May 1984).
Tromans et al., "Accuracy of intraocular lens power calculation in paediatric cataract surgery," Br J Ophthalmol 85:939-941 (2001).
Tseng, et al., "Calculating the optimal rotation of a misaligned toric intraocular lens," J Catactact Refract Surg, Laboratory Science, Oct. 2008, vol. 34, pp. 1767-1772.
Uozato et al., "Intraoperative Confirmation Device for IOL Centering," Folia Ophthalmologica Japonica, vol. 41, 1990, pp. 1325-1329.
Van Heugten, T., et al. "Validation of Novel Hartmann-Moire Wavefront Sensor with Large Dynamic Range", presented at Wavefront Congress, Feb. 17, 2008, available at http://www.wavefront-congress.org/info/listing_detail.asp?absID-12, last visited Feb. 28, 2008.
Villada Jr., et al., "Comparative evaluation of the Allergan Humphrey 570 and Canon RK-I autorefractors: II, Objective autorefraction in pseudophakes", Eye. 1992;6 (Pt 3):287-9 (Abstract).
Walline JJ, "Repeatability and validity of astigmatism measurements", J Refract Surg. Jan.-Feb. 1999; 15(1):23-31 (Abstract).
Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.
Wood IC., "A review of autorefractors", Eye. 1987;1 (Pt 4):529-35 (Abstract).
Yalvac IS, et al., "Calculation of intraocular lens power with the SRK IIformula for axial high myopia" Eur J Ophthalmol. Oct.-Dec. 1996;6(4):375-8 (Abstract).
Zaldivar et al., "Intraocular lens power calculations in patients with extreme myopia," J Cataract Refract Surg 26:668-674 (May 2000).
Canadian Office Action, re CA Application No. 2,561,388, dated May 12, 2014.
International Preliminary Report on Patentability, re PCT Application No. PCT/US13/61729, mailed Oct. 10, 2014.
Nanavaty, et al.: "Anterior capsule cover and axial movement of intraocular lens," Eye (2008) 22, 1015-1023.
Narvaez et al.: "Accuracy of intraocular lens power prediction using the Hoffer Q, Holladay 1, Holladay 2, and SRK/T formulas," Journal of Cataract & Refractive Surgery, Dec. 2006.
CA Office Action re Application Number CA 2,561,388, dated May 27, 2015.

\* cited by examiner

INTEGRATED SURGICAL MICROSCOPE AND WAVEFRONT SENSOR

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57. Specifically, this application is a continuation of U.S. patent application Ser. No. 13/619,168, entitled "INTEGRATED SURGICAL MICROSCOPE AND WAVEFRONT SENSOR," and filed Sep. 14, 2012, which is a continuation of U.S. patent application Ser. No. 13/021,594, entitled "INTEGRATED SURGICAL MICROSCOPE AND WAVEFRONT SENSOR," and filed Feb. 4, 2011, which is a continuation of U.S. patent application Ser. No. 11/110,653, entitled "INTEGRATED SURGICAL MICROSCOPE AND WAVEFRONT SENSOR," and filed Apr. 20, 2005, which claims the benefit of U.S. Provisional Application No. 60/563,727, filed Apr. 20, 2004, each of which is incorporated by reference in its entirety.

BACKGROUND

Refractive surgery and other corrective procedures are commonly performed on the human eye. During a refractive surgical procedure, the refractive quality of the eye is altered. The goal of refractive surgery typically is to correct a defective refractive condition of the eye, while not diminishing the overall refractive quality of the eye. In some cases, the goal is to actually improve the overall refractive quality of the eye.

Refractive measurements are typically taken with phoropters, pachymeters, corneal topographers, autorefractors, keratometers, and/or wavefront sensors. Of these devices, wavefront sensors generally provide the greatest detail about the refractive condition of, and additional information relating to, the eye. Wavefront sensors are generally standalone devices that operate in relatively large areas dedicated to the use of the wavefront sensors. With most existing wavefront sensors, the patient's eye is measured while the patient is in a sitting position.

Many methods of performing refractive eye surgery require pre-operatively measuring the refractive quality of a patient's eye using a wavefront sensor or other measuring device. This refractive quality information is used to plan a detailed refractive surgical procedure. The patient is then typically moved from the wavefront sensor location to a surgical location, where the patient lies supine in the "surgical position." During the refractive surgical procedure, the surgeon may view the patient's eye through a surgical microscope or other viewing device, which typically is suspended above the patient's head via a balancing mechanism or other similar device. Once the refractive surgical procedure is completed, the patient is typically moved back to the wavefront sensor location, and the eye is measured to determine the outcome of the surgery.

Although measuring the refractive quality of the eye after the refractive surgery has been performed provides a quantification of the outcome of the surgery, it does not allow modifications to the surgery to be performed while the patient remains in the surgical position. If the outcome is not ideal, the patient may be relocated to the surgical area for a re-treatment, but in many cases a re-treatment may not be as effective as if the procedure had been performed to produce an ideal result the first time before the patient was moved from the surgical position. Additionally, moving a patient out of the sterile surgical field for diagnostic purposes, and then back into the surgical field, can be problematic.

If the refractive quality of the eye could be measured repeatedly as the surgery is progressing, without moving the patient, the surgeon would have the opportunity to judge whether the procedure was producing desired results at the expected rate, and would be able to make adjustments or course corrections to the procedure midstream to improve the likelihood of achieving the desired outcome. Unfortunately, existing wavefront sensors and other measuring devices are generally relatively large and heavy, making them impracticable or impossible to suspend above a patient's head during surgery. As a result, a patient must be physically moved between wavefront measurement procedures and surgical correction procedures that are typically performed under a surgical microscope.

While attempts have been made to integrate a microscope into a comprehensive treatment and measurement device, such devices are typically very large, heavy, and cumbersome, such that they cannot be practically suspended above a patient lying in the surgical position. These devices also typically include shared lenses and other optical components. The sharing of optical components in this manner generally obscures the overall quality of the measurements that are produced, since each device component typically has its own set of optical requirements that cannot each be optimally satisfied using shared lenses and so forth. Thus, a need exists for an improved device for measuring and evaluating refractive and other optical properties and characteristics of an eye.

SUMMARY

A wavefront sensor is integrated with a surgical microscope for allowing a doctor to make repeated measurements of a patient's eye while the patient remains in a surgical position. The device includes a wavefront sensor optically aligned with a surgical microscope such that their fields of view at least partially overlap. The optional inclusion of lightweight, compact diffractive optical components in the wavefront sensor allows the integrated device to be supported on a balancing mechanism above a patient's head during a surgical procedure. As a result, the need to reposition the device and/or the patient between measuring optical properties of the eye and performing surgical procedures on the eye is eliminated.

Other features and advantages of the invention, including methods of using the device described above, will appear hereinafter. The features of the invention described above can be used separately or together, or in various combinations of one or more of them. The invention resides as well in subcombinations of the features described.

BRIEF DESCRIPTION OF THE DRAWINGS

In the drawings, wherein the same reference number indicates the same element throughout the several views.

DETAILED DESCRIPTION

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Figure 1:
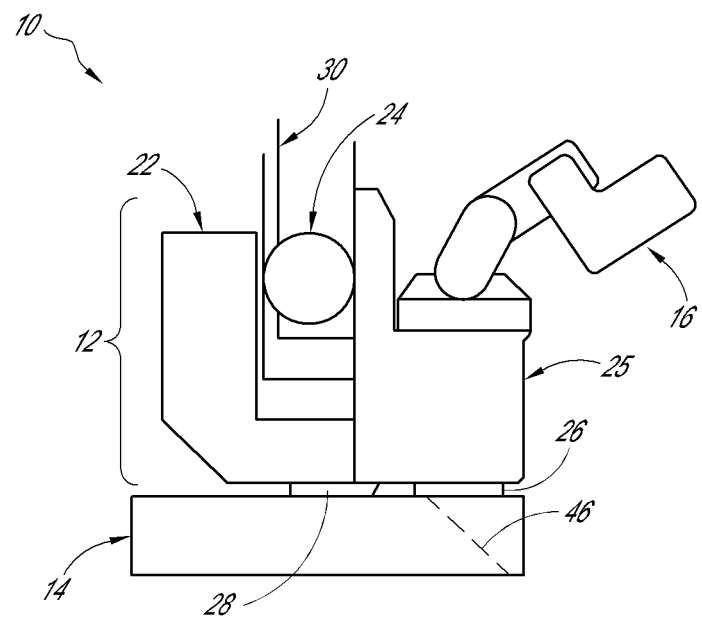
FIG. 1 is a side view of an integrated wavefront sensor and surgical microscope positioned above a patient's head.
Figure 1:
Figure 5:
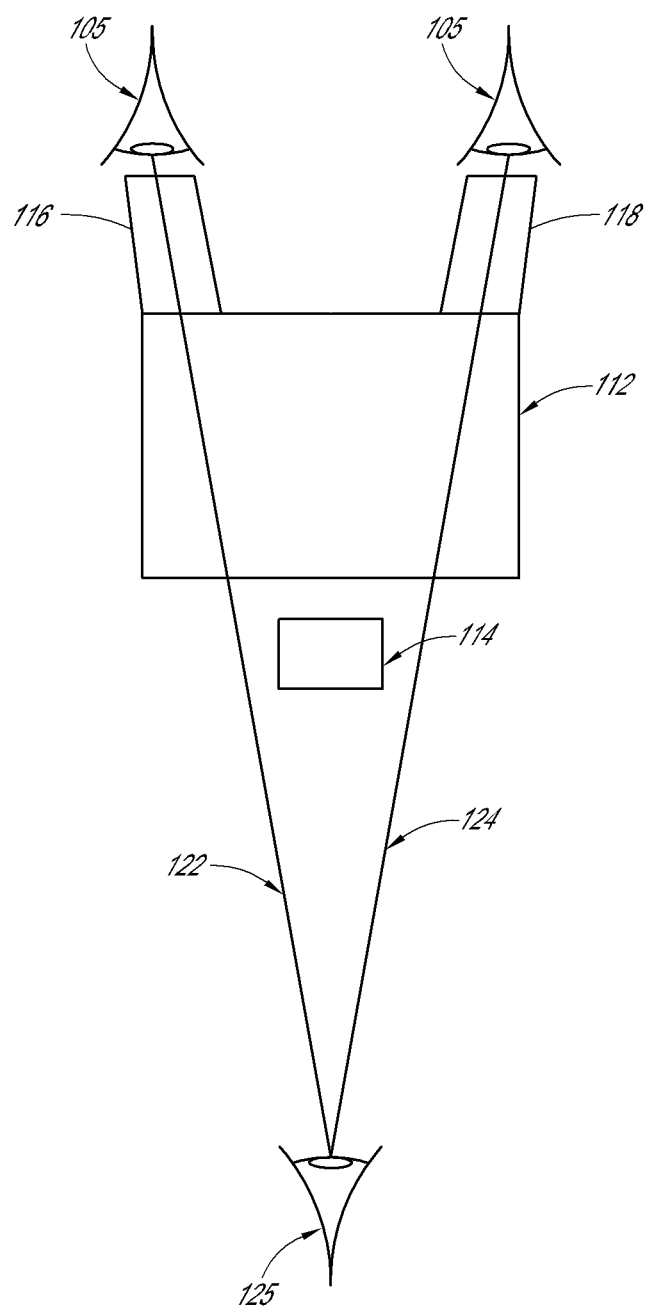
FIG. 5 is a front-view schematic diagram of the operation of the integrated wavefront sensor and surgical microscope illustrated in FIG. 4.

Referring to FIG. 1, a surgical device 10 includes a surgical microscope 12, or other suitable viewing device, attached to a wavefront sensor 14, or other measuring device. The surgical microscope 12 includes an eyepiece 16, or other viewing mechanism, which includes one or more optical channels each having one or more optical lenses therein. The eyepiece 16 is preferably binocular, or stereo, in that it includes two optical channels for allowing a doctor to view an eye 18 of a patient 20 using both of the doctor's eyes (as is best seen in FIG. 5). While a monocular eyepiece may alternatively be used, a binocular eyepiece is generally preferred because it provides a higher quality, more complete view to the doctor.

The surgical microscope 12 preferably further includes a light source 22 for providing visible light into the optical pathway of the eyepiece 16, a focusing knob 24 for adjusting the focus of the microscope 12, and an objective lens 26, or other suitable lens, for focusing light beams. In one embodiment, the objective lens 26 is threaded onto the microscope 12 via internal threads on the lens 26 that match external threads on a body 25 of the microscope 12.

The wavefront sensor 14 may be attached to the microscope 12 in any suitable manner, and is preferably removably attached to the microscope 12. For example, the objective lens 26 may be removed from the microscope 12, and the wavefront sensor 14, which preferably includes an attachment portion with interior threads that match the exterior threads of the microscope body 25, may be screwed onto the external threads of the microscope 12. The objective lens 26 may then be screwed back onto the external threads beneath the attachment portion of the wavefront sensor 14. One or more fasteners 28 may optionally be included to further (or alternatively) secure the wavefront sensor 14 to the microscope 12. The wavefront sensor 14 may alternatively be attached to the microscope via screws, bolts, pins, clamps, adhesive, or any other suitable fasteners or attachment means.

Figure 2:
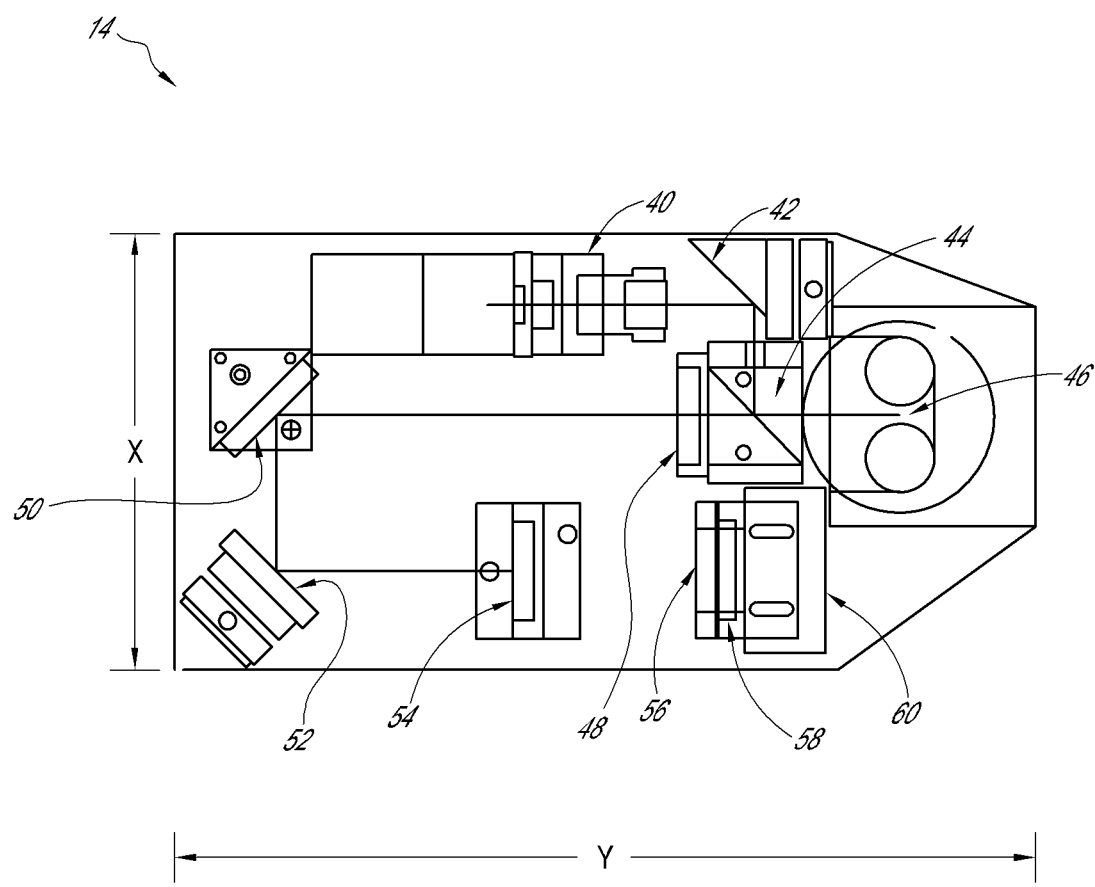
FIG. 2 is a top view of the internal components of a wavefront sensor (with the cover removed) according to one embodiment.

Referring to FIG. 2, the interior of one embodiment of a wavefront sensor 14 is illustrated. The wavefront sensor 14 includes a laser source 40, or other light source, for creating a beam of light, preferably infrared light. During operation, the beam of infrared light is preferably directed by a mirror 42 toward a beam splitter 44 or other suitable device. An aperture-sharing element, such as a combiner mirror 46 (shown in dashed lines in FIG. 1), a beam-splitter, or other similar device, reflects the beam of infrared light down into the eye 18 of the patient 20. The combiner mirror 46 preferably reflects infrared light while transmitting visible light so that a doctor can see the patient's eye 18 while looking through the combiner mirror 46. The combiner mirror 46 may alternatively be configured to reflect a portion of the visible light spectrum, and/or to transmit a portion of the infrared light spectrum, as described below.

After the infrared light beam enters the eye 18, it is reflected, as a wavefront, from the retina of the eye 18 toward the combiner mirror 46. The combiner mirror 46 redirects the light beam through the beam splitter 44 toward a first lens 48. The first lens 48 relays the infrared light beam off of mirrors 50 and 52 toward a second lens 54, which directs the light beam onto a diffractive optical component, such as a first reticle or grating 56. The mirrors 42, 50, 52 are optionally included in the wavefront sensor 14 for re-directing the light beam to maintain it within a compact area, which facilitates the minimization of the overall size and length of the wavefront sensor 14. A greater or lesser number of mirrors may be included in the wavefront sensor 14.

The light beam is diffracted by the first grating 56, as described in detail below, and preferably travels through another diffractive optical component, such as a second grating 58, which further diffracts the light beam and creates a final image of the wavefront reflected from the eye 18. A camera 60, and/or another light detector or sensor, such as a CCD camera or other suitable device, then captures, records, and/or detects the final image of the eye 18 and converts it into a computer-readable format. A computer may then measure and analyze the data to quantify characteristics of the wavefront, and thus, the refractive properties of the eye being examined.

The wavefront sensor 14 may of course include a greater or lesser number of components to meet the requirements of a given system. For example, a greater or lesser number of diffractive gratings or optical lenses may be included in the wavefront sensor 14. Moreover, additional optical components, such as a camera lens, may optionally be included between the second refractive grating 58 and the camera 60. Thus, the specific configuration of the wavefront sensor 14 illustrated in FIG. 2 is only one example a suitable wavefront sensor configuration.

Because the wavefront sensor 14 requires relatively few components, and uses relatively small, lightweight diffractive optical elements in its wavefront analysis section, the wavefront sensor 14 may be very compact and lightweight, and can produce higher resolution and more accurate alignment registration than a wavefront sensor using larger conventional refractive optics, such as a typical Hartmann-Shack wavefront sensor, as described below. The wavefront sensor 14 preferably has a length Y that is less than 10 inches, more preferably less than nine inches, more preferably approximately 8.5 inches, and a width X that is preferably less than 5 inches, more preferably approximately 4.5 inches. The wavefront sensor 14 preferably weighs less than five pounds, more preferably less than 3 pounds or less than 2 pounds. The wavefront sensor 14 may of course be any other suitable size and/or weight.

Due to its relatively low weight and small size, the wavefront sensor 14 may be directly or indirectly attached to the surgical microscope 12 to form an integrated surgical device 10. In this sense, the term "integrated" generally refers to the wavefront sensor 14 and the surgical microscope 12 being incorporated into a unit. The integrated surgical device 10 may be attached to a balancing mechanism, hanging mechanism, or other suitable device or stand for suspending the integrated device 10 over a patient's head during surgery. The balancing mechanism or other supporting device may be spring-loaded, counter-balanced, or otherwise balanced for supporting the integrated device 10. Balancing mechanisms of this nature are commonly used to support and suspend surgical microscopes.

To secure the integrated surgical device 10 to a balancing mechanism, an attachment portion 30 of the surgical microscope 12 (or of the wavefront sensor 14) may be attached to the balancing mechanism via screws, pins, bolts, or other suitable fasteners, or the integrated device 10 may be attached to the balancing mechanism in any other suitable manner. In one embodiment, the wavefront sensor 14 may be added to an existing surgical microscope 12 that is already supported on a balancing mechanism. The field of view and the focal length of the microscope 12 and/or the wavefront sensor 14 may then be adjusted, if necessary, to optically align the devices relative to one another, as further described below.

Generally speaking, refractive optical components are used to redirect a light beam as it passes through a material having a higher density than air, such as a glass refractive lens. Diffractive optical components, conversely, are used to bend a light beam as it encounters the sharp edges of an element, such as the gratings 56, 58, and only portions of the light beam occurring near the edges of the grating or other object are redirected. Diffractive optical components, such as gratings, are typically significantly smaller and weigh less than refractive optical components, such as refractive lenses.

The one or more diffractive gratings used in the wavefront sensor 14 may be made of any suitable material. A preferred diffractive grating is made from a clear material, such as glass, and has equally spaced perpendicular lines etched or otherwise present on its surface. The grating may include, for example, a repeating sequence of solid lines each having a width of approximately 12.5 microns, with each pair of lines separated by approximately 12.5 microns of clear glass (the lines and glass spaces on the grating may of course have any other suitable dimensions). The same sequence is repeated with lines running perpendicularly to the first set of lines, such that a pattern similar to that of a standard grid (i.e., a network of uniformly spaced horizontal and perpendicular lines) is formed.

Figure 3:
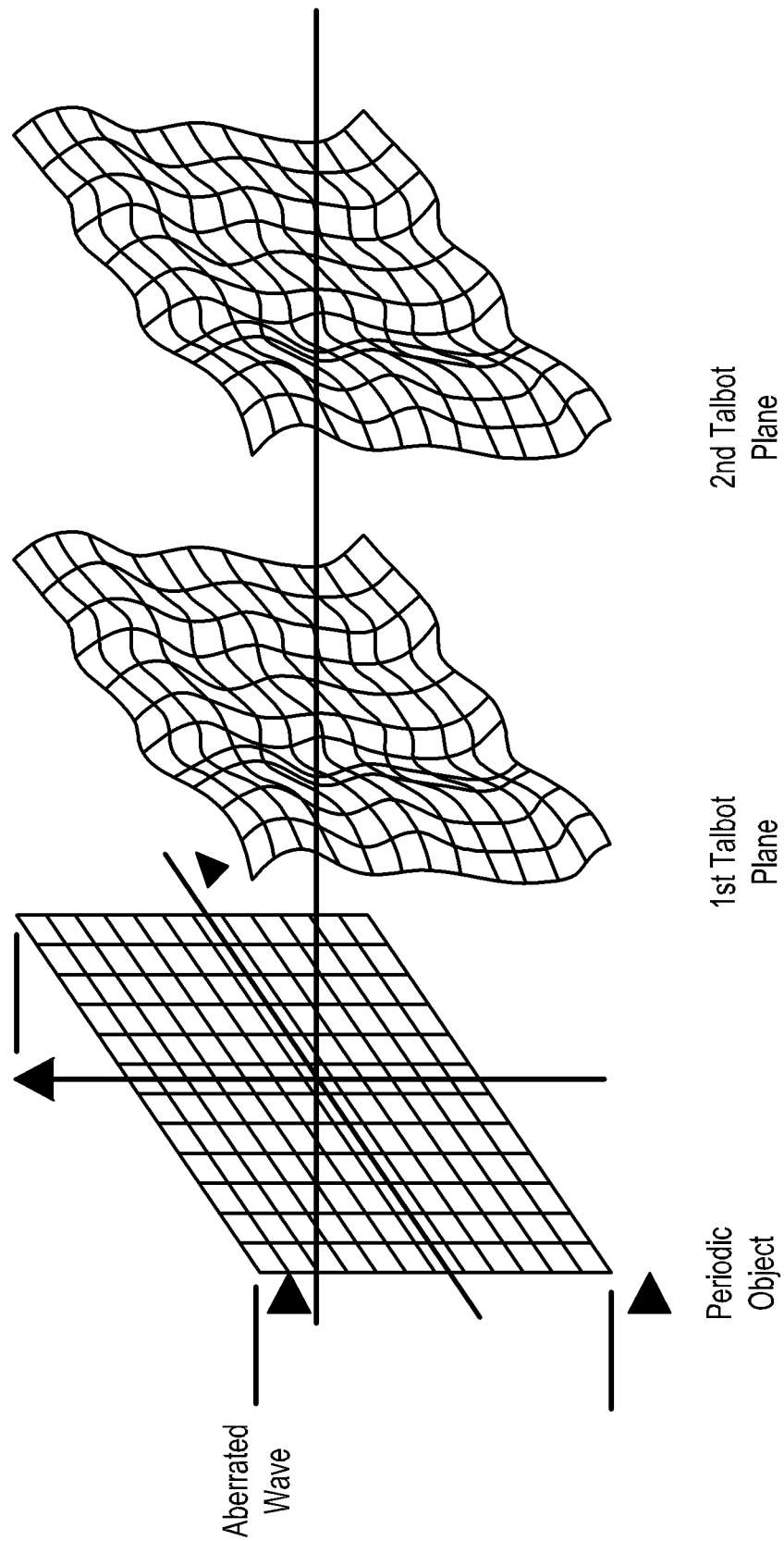
FIG. 3 is a perspective view of an aberrated wave traveling through a grating, as well as wave images produced at the first and second Talbot planes of the grating.

As illustrated in FIG. 3, when a wavefront of light reflected from an eye encounters a grating (referred to as the "Periodic Object" in FIG. 3) diffractive effects begin to occur. Some of the light hits the solid portions of the lines on the grating and is prevented from passing through the grating. Some of the light passes cleanly through the clear spaces in the grating and is not affected by the grating lines. The remaining light, however, encounters the edges of the solid lines as it passes through the grating. This light is disturbed by the lines and is deflected away from the central core of the light that passes cleanly through the clear spaces in the grating.

This redirected light encounters light that has been redirected by one or more adjacent grating lines. When portions of light directed from equally spaced lines meet one another, a phenomenon known as the "Talbot Effect" occurs, and a series of dark and light zones form in a space within a predictable distance downstream from the grating, at locations referred to as Talbot planes. This phenomenon is described in detail in U.S. patent application Ser. No. 10/885,504, filed Jul. 6, 2004, as well as in "Fourier Transform Method For Automatic Processing of Moire Deflectograms," Quiroga et al., Opt. Eng. 38(6) pp. 974-982 (June 1999), and in "Refractive Power Mapping of Progressive Power Lenses Using Talbot Interferometry and Digital Image Processing," Nakano et al., Opt. Laser Technology. 22(3), pp. 195-198 (1990), all of which are incorporated herein by reference.

If the wavefront of light that passed through the grating is a flat, plane wave, the dark and light zones form a perfect replica of the grating, i.e., a virtual image of the grating. If, however, the wavefront is aberrated or includes any deviations from a flat, plane wave, the shape and size of the virtual image of the grating is distorted, as shown in FIG. 3. By observing the distortions in the shape and size of the virtual image created by the grating, the characteristics of the wavefront can be determined. The virtual image may be observed by a camera or other light detector, and the images may be measured, typically by a computer, to accurately quantify the characteristics of the wavefront, and hence, the refractive properties of the eye being examined.

In one embodiment, two or more gratings are aligned in series in the wavefront sensor. By causing the virtual image to pass through the line patterns in one or more additional gratings, the virtual image of the grating is modified to show less resolution, which can compensate for a camera having insufficient resolution. Additionally, by adding one or more gratings, and rotating the downstream gratings with respect to one another, the changes in the virtual image of the initial grating are visually converted into rotational movement, rather than just shrinkage or expansion, and the characteristics of the wavefront may be determined without change in size of the virtual image.

The virtual image created by the gratings contains, simultaneously, two sets of information. The first set of information is the virtual image of the grating from which the refractive properties of the eye are characterized, as described above. The second set of information is an almost complete image of the pupil of the eye, which is comprised of the light that passed untouched through the clear spaces of the grating, as well as light that reflected from the surface of the pupil, the sclera, the limbus, and/or other features of the eye if additional illumination is directed to illuminate these features. This image essentially appears to be that of an eye being observed with a grid (i.e., a network of uniformly spaced horizontal and perpendicular lines) between the eye and the observer.

Figure 4:
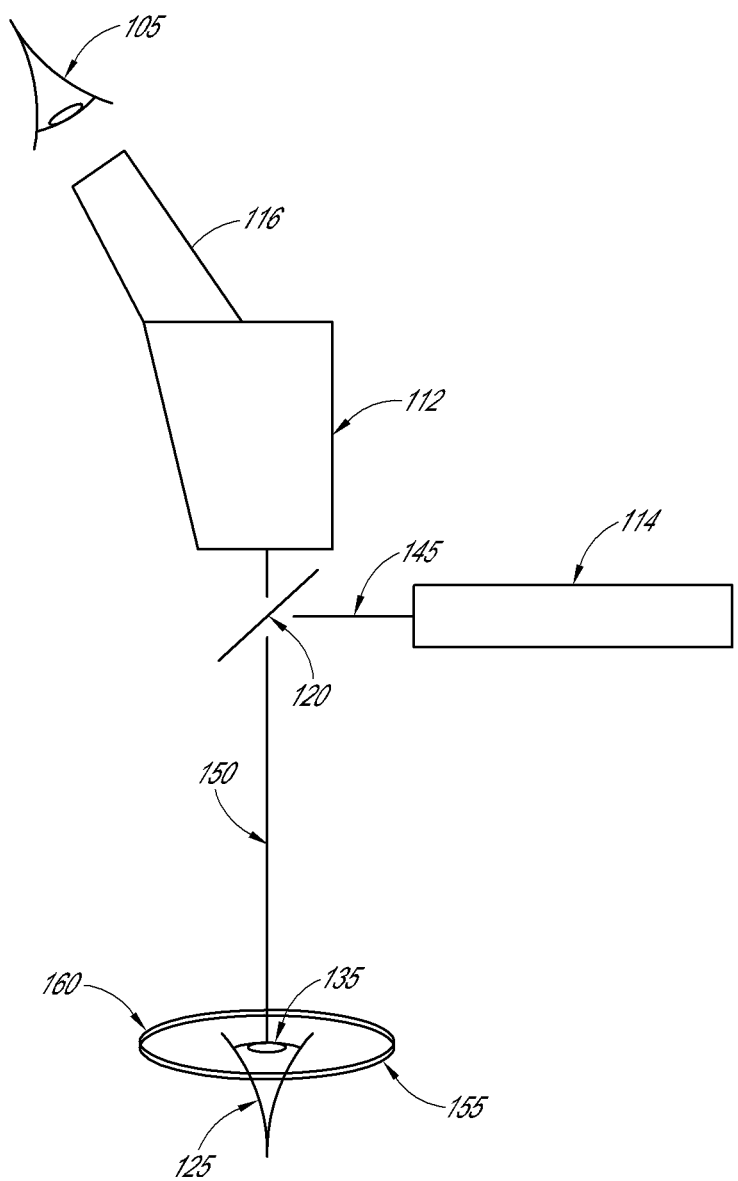
FIG. 4 is a side-view schematic diagram illustrating the operation of an integrated wavefront sensor and surgical microscope according to one embodiment.

Referring to FIGS. 4 and 5, a schematic representation of a process for measuring characteristics of an eye is shown. A surgeon (or other doctor) 105 looks through a surgical microscope 112 at the eye 125 of a patient. The surgical microscope 112 preferably includes binocular, or stereo, optics such that it includes two optical viewing channels 116, 118 (as shown in FIG. 5). A monocular microscope may alternatively be used, however. Visible light reflecting from the patient's eye 125 travels along a light pathway 150, passes through a combiner mirror 120 or similar device, and into the microscope 112, so that the surgeon may view the patient's eye 125 along visual pathways 122, 124.

A wavefront sensor 114 generates an infrared light beam and projects it outwardly along a pathway 145 toward the combiner mirror 120. While the combiner mirror 120 is shown located outside of the wavefront sensor 114 in the schematic representation of FIGS. 4 and 5, it is understood that the combiner mirror 120 may be located inside the wavefront sensor 114, as is shown in FIGS. 1 and 2, or in any other suitable location where the optical pathways of the surgical microscope 112 and the wavefront sensor 114 meet.

The combiner mirror 120 is preferably transparent to visible light but reflective to infrared light so that it reflects the infrared light beam toward the patient's eye 125. The wavefront sensor 114 and the microscope 112 preferably share a common aperture through the combiner mirror 120. Alternatively, a beam splitter that transmits and reflects both a portion of the visible light and a portion of the infrared light may be used in place of the combiner mirror 120. Using such a beam splitter would allow the wavefront sensor 114 to operate at a wavelength other than that of the infrared light, such as at a wavelength in the visible spectrum.

In another embodiment, the combiner mirror 120 may be configured to reflect a portion of the visible light spectrum, allowing the wavefront sensor 114 to operate in a wavelength range within the visible spectrum, yet prevent that particular wavelength from entering the Microscope 112. In yet another alternative embodiment, the combiner mirror 120 may be a narrow pass/reflect combiner, which reflects only a defined wavelength of light having a lower and upper range, thereby allowing the wavefront sensor 114 to operate within the visible light spectrum. The defined visible light spectrum would then be selectively blocked from returning to the microscope 112, while all light above or below the lower and upper ranges would be freely transmitted.

The combiner mirror 120 reflects the light beam along pathway 150 toward the patient's eye 125. The infrared light enters the patient's eye 125 and is reflected as a wavefront back along light pathway 150 toward the combiner mirror 120, which reflects the wavefront along light pathway 145 into the wavefront sensor 114. The wavefront sensor 114 then measures the wavefront using the process described above, or using a similar process. The wavefront sensor 114 may have the same configuration and components as the wavefront sensor 14 illustrated in FIG. 2, or it may have an alternative configuration and may include alternative components.

The wavefront sensor 114 and the microscope 112 are each preferably focused at a point occurring at plane 135, such that a field of view 155 of the wavefront sensor 114 at least partially overlaps a field of 160 of the microscope 112. During measuring, viewing, and/or performing surgery, the patient's eye 125 is preferably located within the overlapping portion of the fields of view 155, 160. In a preferred embodiment, the wavefront sensor 114 and the microscope 112 are focused at substantially the same point, such that the center of each field of view 155, 160 is located at approximately the same point, in the same plane 135, preferably at or near the center of the patient's eye 125.

As a result, the surgeon 105 may look through the microscope 112 directly into the visual axis of the patient's eye 125 while the wavefront sensor 114 takes measurements of the eye 125. Furthermore, because the fields of view 155, 160 overlap at the patient's eye 125, the patient does not have to change the gaze angle of the patient's eye 125 at any time during the viewing and measurement processes. This can be very advantageous, especially when the surgical procedure being performed prevents the patient from seeing clearly, or at all, such that it is nearly impossible for the patient to accurately adjust the gaze angle of the patient's eye 125 according to a surgeon's instructions.

The integrated wavefront sensor and surgical microscope described herein provides several advantages. First, it allows a surgeon or other doctor to directly view a patient's eye while the wavefront sensor performs measurements of the refractive characteristics or other optical properties of the patient's eye. As a result, a surgeon can view the results of a given step of a surgical procedure without having to move the patient, the patient's eye, or the device. Indeed, the gaze angle of the patient's eye does not need to change at all during the viewing and measuring steps, and the surgeon's view may be directly aligned with, as opposed to offset from, the visual axis of the patient's eye.

Additionally, due to the relatively small number of components used in the wavefront sensor, and the relatively small size and low weight of those components, particularly of the one or more lightweight diffractive gratings or other diffractive optical components, the integrated device may be very compact. Accordingly, the lightweight integrated device can be suspended on a balancing device, or other supporting mechanism, above the head of a patient lying in the supine surgical position, while the surgeon views the patient's eye through the surgical microscope of the integrated device.

To maintain its compact size and design flexibility, the integrated surgical device 10 is preferably not integrated with or otherwise attached to a refractive laser device or other refractive surgical tool. Thus, the integrated surgical device 10 is preferably used primarily for viewing and measuring purposes, while one or more surgical tools used to perform corrective eye procedures are physically separate from the integrated device. Lightweight or otherwise compact surgical tools, however, may optionally be incorporated into the surgical device 10. The wavefront sensor 14 and the surgical microscope 12 also preferably do not share an optical pathway to the patient's eye 18 with any other surgical devices.

Because the wavefront sensor and the surgical microscope are preferably (although, not necessarily) separate components that are removably attached to one another, they may each include their own optical components, including any lenses. Thus, the wavefront sensor and the surgical microscope do not need to share a lens, thus providing several advantages and general design flexibility over integrated surgical systems that require one or more lenses to be shared between two or more optical components.

Some surgical systems, for example, use a common optical lens to focus light beams from both a wavefront sensor and a refractive laser device. By sharing a lens in this manner, the flexibility to select or design the lens for only a single specific function is lost, as is the ability to design the best possible lens for the overall system application. By using a common lens, compromises must be made to meet the requirements of each component that shares the lens.

Antireflective coatings, for example, are commonly applied to lenses so that they can function optimally within a certain wavelength. If the laser being used is of a different wavelength than the wavefront sensor illumination beam, however, a common antireflective coating cannot be selected that will work optimally for each of the wavelengths. The same holds true for the wavelength of the wavefront sensor illumination beam in comparison to that of the visible light used to provide visibility through a microscope. Because the surgical device 10 described herein does not require that a lens be shared between the wavefront sensor and the surgical microscope, different antireflective coatings may be applied to the lenses of each of these components, thus allowing for optimal coatings to be selected for each component.

Another disadvantage of sharing a common lens between two or more optical components is the inability to select an optimal focal length, or power, of the lens for each component involved. In many cases, a long focal length lens is desirable in a wavefront sensor to provide sufficient working space for a doctor between the wavefront sensor and the patient. With many refractive lasers, conversely, a shorter focal length lens is desirable to more tightly focus the laser energy into a shorter plane. A system that shares a common lens for these components must compromise or settle on a common focal length, which will not be optimal for one or both of the components.

Additionally, if a wavefront illumination beam is projected through a lens that is also used as an imaging lens for a microscope, a high likelihood of "flashback glint" arises. Even when an optimal antireflective coating is applied to a lens (which likely cannot be achieved for a lens shared by multiple components, as described above), a certain amount of light will reflect from the lens surface as the light enters the lens. This light reflects back into the wavefront sensor, and is seen as a tiny bright flash of light, or "glint." This glint can obliterate the wavefront information of one or more portions of the eye. Thus, an advantageous feature of the surgical device 10 is that it does not require a lens to be shared by the wavefront sensor 14 and the surgical microscope 12.

Other advantages result from the detachable nature of the integrated wavefront sensor and surgical microscope, as compared to existing devices that are permanently integrated. For example, the option of adding the compact wavefront sensor 14 to an existing surgical microscope 12, or of moving the wavefront sensor 14 from one surgical microscope 12 to another, or of removing the wavefront sensor 14 from the surgical microscope for another reason, such as to individually repair one of the devices, provides a great deal of flexibility. A cost benefit may also be achieved, particularly if a component becomes defective, since it is likely cheaper to replace or repair only one of the wavefront sensor 14 and the microscope 12, than to replace an entire permanently integrated system.

The surgical device 10 may be used to improve and/or enhance a variety of corrective procedures performed on the eye. In general, by providing the ability to measure the refractive characteristics or other optical properties of a patient's eye while the patient remains lying in a surgical position, several of the limitations of existing systems may be overcome. Several examples of corrective eye procedures that may be enhanced by using the surgical device 10 are described below.

Cataract surgery generally involves replacing the natural lens of an eye after the natural lens has become unclear. Existing methods typically require measuring the physical dimensions of the eye with ultrasound, followed by calculating the refractive power of the artificial lens, or other replacement lens, to be inserted. Because the natural lens is unclear, these measurements are often difficult to make. Additionally, variations in the structures of the eye that cannot typically be measured using existing techniques may degrade the calculation.

The integrated surgical device 10 facilitates measurement of the eye's refractive power before and/or immediately after the natural lens is removed, without movement of the patient or the patient's eye, such that the true refractive power of the eye can be more accurately determined. For example, if it is determined that 42 diopters of power are needed for a patient to see clearly at a predetermined distance, and after the natural lens is removed the eye has only 22 diopters of power, then it can easily and accurately be determined that 20 diopters of power must be introduced to the eye via the new lens being inserted.

With existing systems, once the lens is removed, and the doctor wishes to make a wavefront measurement, the patient typically has to be moved from the surgical table to a measurement device to make the refractive measurements. Because the patient is typically sedated, and there may be an incision in the patient's eye, and there are sterility requirements to maintain, it is not practical to move the patient between surgical steps. By using the integrated surgical device 10, which is preferably suspended above the patient's head, conversely, a surgeon may view the patient's eye through the surgical microscope 12 while the wavefront sensor 14 makes measurements of the eye with the natural lens removed. Accordingly, the patient, as well as the patient's eye, is able to remain motionless in the surgical position during the entire corrective process.

A further challenge associated with cataract surgery is that once the replacement lens is inserted into the eye, the replacement lens must be aligned to ensure that it is properly oriented and positioned. If, for example, the replacement lens is not correctly centered, or is not perpendicular to the optical axis of the eye, or if the cylindrical portion (if astigmatic correction to the replacement lens is also being performed) is not oriented to the correct axis, refractive aberrations may be introduced, and the surgical outcome will therefore be degraded. The integrated surgical device 10 allows the surgeon to make refractive measurements of the eye, after the replacement lens has been inserted, which may be used to guide any required repositioning of the replacement lens.

Additionally, during cataract surgery, viscoelastic cushioning fluids are typically injected into the eye to protect endothelium cells and other structures, and should be completely removed after the surgery is completed. The wavefront sensor 14 may be used to identify any remaining viscoelastic pockets (as wave distortions), and can therefore assist the surgeon in removing all of the viscoelastic fluid.

By using the integrated surgical device 10, astigmatisms may also be reduced during the lens replacement procedure by means other than using a replacement lens with a cylinder component. For example, the location and size of any entry wound could be adjusted, the position of a paracentesis incision could be adjusted, as could any additional lamellar, radial, or arcuate cuts made, all while the surgeon receives feedback from the wavefront sensor 14 that may guide corrections made during the procedure.

Additionally, if a replacement lens is damaged during insertion, due to overstress during gripping, nicks and cuts in the lens surface, or damage to the centering haptics, wavefront measurements made after the insertion can identify the damage. Accordingly, the replacement lens may be replaced or repaired before the membrane that previously contained the natural lens shrinks and tightens onto the replacement lens.

A process of introducing relaxing incisions into various locations of the eye, which causes the cornea to flatten out in predictable directions, is often used to eliminate astigmatism of the cornea. Such a procedure is often performed at the end of cataract surgery, for example, to eliminate an astigmatism that was induced by the main cataract incision, or that had previously existed. The amount of flattening generally varies from patient to patient, however, and is therefore very difficult to precisely predict. By using the integrated surgical device 10, the wavefront sensor 14 can make measurements during the surgical procedure to guide the position, depth, and length of incisions made by the surgeon to achieve desired results.

Corneal transplant surgery, in which a small central portion, typically 8 to 10 mm in diameter, of the cornea is cut from a donor's eye and grafted into a correspondingly-sized hole cut into a recipient's cornea, may also be improved by using the integrated surgical device 10. During the positioning and suturing of the donor's corneal tissue into the recipient's cornea, refractive errors are typically difficult to measure. Refractive errors may be introduced if, for example, the donor's corneal tissue is not properly centered, rotated, or oriented in the recipient's cornea, or if the sutures are too tight, too loose, or not evenly tightened. If the recipient's eye is measured after the healing process has completed, refractive errors are difficult, if not impossible, to correct.

By using the integrated surgical device 10, a surgeon may measure refractive changes in the eye while placing and suturing the donor graft. Indeed, the recipient may remain lying on the surgical table, and the surgeon may look directly into the visual axis of the recipient's eye, while the refractive measurements are being taken. Accordingly, the recipient does not need to be moved at any point during the transplant procedure. Additionally, the donor cornea may be measured by the wavefront sensor to locate its optical axis to assist with better cutting and/or placement of the cornea.

The integrated surgical device 10 may also be used to enhance LASIK (Laser-Assisted In Situ Keratomileusis) refractive surgery, or other laser-assisted surgical procedures. Several variations of laser vision surgery require that a flap be cut from the surface of the cornea to expose the stroma of the cornea to laser treatment. The laser reshapes the stroma to a desired contour, after which the flap is replaced over the reshaped stroma. If the flap is not precisely repositioned at its original location, if foreign matter is trapped inside the flap, if a wrinkle is introduced during repositioning, and/or if a host of other repositioning errors occur, then the visual outcome of the procedure will be degraded. The integrated surgical device 10 allows a surgeon to measure the refractive or optical properties of the eye while the surgeon directly observes the eye, and while the flap is being repositioned, so that any positioning errors or other problems can quickly be corrected.

The integrated surgical device 10 may also be used during a Conductive Keratoplasty ("CK") procedure. CK is a refractive surgical procedure in which highly localized energy pulses, such as heat pulses or radio frequency pulses, are applied to the collagen or stroma of the cornea to reshape the cornea to correct for refractive errors, particularly hyperopia. Current methods typically require that the eye be measured with a conventional refractive device, which provides information regarding how many energy pulses are required to reshape the cornea as desired and identifies which regions of the cornea should receive pulses. The patient is then moved to a surgical location where the energy pulses, typically 8 or more, are applied to the cornea, after which the patient is moved back to the measurement device so that the eye may be re-measured.

The outcome of such a procedure is generally the result of a best prediction, and the actual outcome is rarely exactly as desired due to variability in the response of each individual cornea. If the cornea is under-corrected, more pulses may be added later, but if the cornea is over-corrected, it is difficult, and sometimes impossible, to reverse the over-correction.

By using the integrated surgical device 10, the eye's refractive condition may be measured after each pulse is applied (preferably after a certain minimum number of pulses have been applied, for example, after 6 pulses have been applied, since a complete correction will typically not occur until at least a certain minimum number of pulses have been applied), and the surgeon may therefore make guided corrections during the surgical procedure. The surgeon may, for example, alter the position, size, quantity, and/or energy of the pulses applied if measurements taken between successive pulses dictate that such steps should be taken. Additionally, the placement of the pulses is critically important, and the wavefront sensor may be used to help guide the placement of each energy pulse.

A procedure for positioning an inlay in a cornea along the eye's visual axis may also be aided by using the integrated surgical device 10. In such a procedure, after a flap is created over the cornea, either via a LASIK procedure or another procedure, an opaque disk or similar structure with a small central aperture is placed in the cornea and trapped inside the flap. The inserted disk creates the effect of a smaller aperture, resulting in the depth of view of the eye being increased. It is, however, extremely difficult to center the disk about the eye's visual axis. By using the integrated surgical device 10, the wavefront sensor 14 can make measurements to determine the exact location of the eye's visual axis while the surgeon directly views the eye, which aids the surgeon in precisely positioning the disk in the proper central location.

In an alternative embodiment, the corneal inlay's central aperture may be cut into the inlay by the laser after it has been placed in the eye. In such a case, the precise measurements of the wavefront sensor, coupled with the precise control of the laser placement, may result in a more accurate aperture position than if it were manually positioned.

The integrated surgical device 10 may also be used to control corneal distortion during placement of inserts into the cornea. In the case of myopia, for example, the cornea is too steep and must be flattened. In a typical corrective procedure, slices are cut into the cornea, after which tiny, curved strips are slid into the stroma of the cornea to exert a straightening force on the cornea that flattens the cornea. By using the integrated surgical device 10, the wavefront sensor 14 can make measurements of the eye while the doctor directly views the eye, allowing the doctor to monitor the degree of flattening and to adjust the process (e.g., to add more or different inserts) midstream.

The integrated surgical device 10 may further be used to measure and view the eye during a procedure for adjusting the tension of the ciliary muscle and/or the ciliary process of the eye. In a typical ciliary-tensioning procedure, rings or other devices are inserted into the sclera just beyond the limbus of the eye to exert a radially outwardly pulling force on the ciliary muscle. The goal of this procedure is to expand the relaxed diameter of the ciliary muscle, which in turn provides added tension in the ciliary muscle and removes some of the slack that has developed therein over the years. By using the integrated surgical device 10, the wavefront sensor 14 can take measurements of the eye while the tensioning procedure is being performed under the surgical microscope 12, thus guiding the amount of tensioning required to achieve desired results.

Another corrective procedure involves removing tissue from the cornea, via mechanical slicing or another method, to modify the shape of the cornea. In one embodiment of mechanical tissue removal, an incision is made in the side of the cornea to provide a split in the stroma of the cornea. A shallow spoon-shaped device is then guided into the split, and a blade is used to remove tissue below the spoon's edge plane, resulting in less corneal tissue thickness centrally than peripherally, and thus, corneal flattening (i.e., reduction in myopia). By using the integrated surgical device 10, the wavefront sensor 14 can make measurements during the surgical procedure to guide the process and aid the surgeon in determining how much tissue, at which locations, should be removed.

The natural lens of the eye may also be modified to correct refractive defects in the natural lens. Some defects that may occur over time include small opacities, protein buildup, and size increases in the lens. One method of modifying the natural lens involves removing tissue from the lens to correct vision loss associated with these and other defects. Even a small amount of material removal, however, can result in a large change in refraction. By using the integrated surgical device 10, the wavefront sensor 14 can make measurements during the surgical procedure to guide the process and aid the surgeon in determining how much lens tissue, at which locations, should be removed.

Optical properties of the natural lens may also be modified by introducing chemicals, or changing blood sugar levels, in a patient's system. Using the integrated surgical device 10 during such a procedure allows a surgeon to measure the amount of change resulting from the introduction of one or more chemicals, which can aid the surgeon in reaching a desired outcome.

The integrated surgical device 10 may also be used to aid in controlling or influencing the resulting shape of a lens that is injected into the eye as a liquid and that cures into a solid. Such a lens is commonly referred to as a "form in the bag" lens. Extreme precision is required to attain the desired resultant shape of the lens using such a procedure. During the time period when the material changes from a liquid into a solid, the shape and index of refraction of the lens can be manipulated. Using the integrated surgical device 10 allows a surgeon looking through the microscope 12 to obtain wavefront data about the lens as it is being formed so that proper course corrections can be made during the curing process.

Advancements have been made in the ability to modify or tune the characteristics of an artificial lens after the lens has been inserted into the eye and the eye has healed. By using the integrated surgical device 10, a surgeon viewing the eye through the microscope 12 can make modifications to the artificial lens while the wavefront sensor 14 makes measurements that can guide the procedure.

Several lenses are available that may be inserted into the eye, while the natural lens remains in place, to modify refractive characteristics of the eye. The correct placement of such a lens is critical to achieving a desired outcome. The integrated surgical device 10 allows a surgeon to view the eye while making wavefront measurements, which aids the surgeon in selecting an appropriate lens and in positioning the lens in the correct central location along the visual axis of the eye. Additionally, the integrated surgical device 10 can verify the overall success or failure of the procedure, which allows the surgeon to make adjustments, while the patient remains on the surgical table, if the outcome is not ideal. This not only improves efficiency, but also allows re-accessing of an incision before it has healed, such that a new incision is not required to make corrections after a non-ideal outcome.

Another corrective procedure involves adding material into the cornea, measuring the resulting refractive condition of the eye, then removing a portion of the inserted material to achieve a desired result. The wavefront sensor 14 of the integrated surgical device 10 may be used to measure the eye before the procedure to help determine a minimum amount of material to add, and may also be used to measure the eye after the material is inserted. The wavefront sensor 14 may then be used to measure the eye at various points of the procedure, which is performed under the surgical microscope 12, to ensure that the correct amount of material is removed.

During many existing procedures, a patient's eye is measured with a wavefront sensor at a first location, a treatment is calculated and/or planned based on the measurements, and the patient is then moved to a second location where the actual treatment is performed. Typically, the eye is measured while the patient is sitting upright, but the treatment is performed while the patient is lying facing upward in a supine position. When the patient moves from the upright position to the supine position, the patient's eyes rotate, or "cyclotort." To compensate for this cyclotortion, dye marks are typically placed on the eye while the patient is in the upright position so that the amount of cyclotortion can be measured. By using the integrated surgical device 10, the wavefront measurements may be taken while the patient lies in the supine position, with the cyclotortion present, and while the doctor is viewing the eye. Accordingly, the intermediate step of marking the cornea and compensating for the rotation is not required. The elimination of this step improves the efficiency of the process, and the precision of the orientation of the wavefront registration to the eye is enhanced.

While several corrective procedures have been described herein, it is understood that the integrated surgical device 10 may be used to enhance any vision correction procedure by providing a surgeon the ability to view the eye simultaneously with making wavefront measurements of the eye. Thus, the surgeon may make wavefront measurements while the patient remains lying in the surgical position, and may course adjustments to a procedure midstream without having to move the patient between surgical steps.

While several embodiments have been shown and described, various changes and substitutions may of course be made, without departing from the spirit and scope of the invention. The wavefront sensor 14, for example, could include a greater or lesser number of components arranged in any conceivable configuration. The invention, therefore, should not be limited, except by the following claims and their equivalents.

What is claimed is:

1. A surgical device for measuring properties of an eye, comprising:
a wavefront sensor for performing refractive measurements of the eye, the wavefront sensor comprising one or more fasteners to removably attach the wavefront sensor below a stereo surgical microscope having a support structure to movably support the stereo surgical microscope over a patient's eye, the stereo surgical microscope for providing a field of view,
wherein the one or more fasteners support the wavefront sensor in position relative to the stereo surgical microscope along an optical pathway from the stereo surgical microscope to the eye when the wavefront sensor is attached to the stereo surgical microscope, the optical pathway being shared by the stereo surgical microscope and wavefront sensor, and such that the wavefront sensor is fixedly optically aligned with the stereo surgical microscope,
wherein the wavefront sensor is configured to not substantially alter the focal length of the stereo surgical microscope when attached thereto.

2. The surgical device of claim 1, wherein the wavefront sensor is adapted to attach to the surgical microscope at a position that is between the surgical microscope and a patient during cataract surgery.

3. The surgical device of claim 1, further comprising a combining optical element positioned to receive light that reflects from the eye and to send a first portion of the light reflected from the eye to the surgical microscope, and to send a second portion of the light to one or more optical elements of the wavefront sensor.

4. The surgical device of claim 3, wherein the combining optical element comprises a combiner mirror or a beam splitter.

5. The surgical device of claim 1, wherein the wavefront sensor comprises one or more diffractive optical elements.

6. The surgical device of claim 5, wherein the one or more diffractive optical elements comprise a first grating and a second grating separated by an integer multiple of a Talbot distance, the first and second gratings being rotated with respect to one another.

7. The surgical device of claim 1, wherein the surgical microscope comprises binocular optics.

8. A surgical device comprising:
a wavefront sensor configured to be removably attached to a surgical microscope, the wavefront sensor for performing refractive measurements of the eye, the wavefront sensor comprising a housing having an optical passageway therethrough, and a combining optical element located in the housing along the optical passageway, wherein the combining optical element is positioned to receive light that reflects from the eye and to send a first portion of the light reflected from the eye outside the housing to a surgical microscope via the optical passageway through the housing, and to send a second portion of the light reflected from the eye to one or more optical components within the housing, wherein the wavefront sensor is configured to not substantially alter the focal length of the surgical microscope when attached thereto.

9. The surgical device of claim 8, wherein the combining optical element comprises a combiner mirror or a beam splitter.

10. The surgical device of claim 8, wherein the combining optical element is configured to send light in the visible spectrum to the surgical microscope and to send light in the infrared spectrum to the one or more optical components within the second housing.

11. The surgical device of claim 8, wherein the housing of the wavefront sensor is adapted to attach to a separate housing of the surgical microscope.

12. The surgical device of claim 11, wherein the housing of the wavefront sensor comprises a fastener for removably attaching to the housing of the surgical microscope.

13. The surgical device of claim 8, wherein the wavefront sensor comprises a first grating and a second grating separated by an integer multiple of a Talbot distance, the first and second gratings being rotated with respect to one another.

14. The surgical device of claim 8, wherein the surgical microscope comprises binocular optics.

* * * * *